US00PP08383P

United States Patent [19]

Klemm

[11] Patent Number: Plant 8,383

[45] **Date of Patent: * Sep. 21, 1993**

[54] GERANIUM PLANT NAMED OSNA

[75] Inventor: Siegfried Klemm, Stuttgart, Fed. Rep. of Germany

[73] Assignee: Selecta Klemm, Stuttgart, Fed. Rep. of Germany

[ * ] Notice: The portion of the term of this patent subsequent to Jun. 21, 2008 has been disclaimed.

[21] Appl. No.: 480,091

[22] Filed: Feb. 14, 1990

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new and distinctive geranium plant variety particularly distiguished by its tetraploid dark leaves, which provide a dramatic contrast to its bright vermilion colored flowers. The huge flower clusters are long lasting and are supported by strong upright 23-24 cm. stalks, whose foliage is bushy and botrytis-resistatnt. The florets contain five petals, which when open resemble windmills.

1 Drawing Sheet

BACKGROUND

My new geranium cultivar originated as a seedling of unknown parentage in the nursery at Ornasbruck, West Germany. The seedling bloomed for the first time in 1980, and has been reproduced by me in my nursery in Stuttgart, West Germany by means of cuttings. Propagating several generations of this plant has conclusively shown the consistency of its unique characteristics throughout the generations and appear to be firmly fixed.

DESCRIPTION OF THE DRAWINGS

My new variety of geranium is illustrated in the accompanying photographic drawing. Shown in the drawing are huge vermilion-colored floret clusters, surrounded by contrasting dark green foliage. The colors of the foliage and flowers being as near true to that specified as is reasonable possible to obtain by conventional photographic procedures.

DESCRIPTION OF THE NEW PLANT

The following is a detailed description of my new geranium variety OSNA as observed of plants grown both in my greenhouse and outdoors at Stuttgart, with the color designation being according to the R.H.S. Colour Chart published by The Royal Horticultural Society of London, England.

THE PLANT

Origin: Seedling.
Parentage: Unknown.
Clasification:
*Botanic.*—*Pelargonium zonale* hybrid.
*Commercial.*—Geranium.
Form: Round-shaped bush.
Growing rate: Medium to Rapid.
Branching character: Medium.
*Flower stems.*—About 24 cm. long.
Growth habit: Upright.
*Strength.*—Medium.
Foliage:
*Quantity.*—Medium.
*Shape of leaf.*—Round.

*Size.*—Medium to Large.
*Texture.*—Leathery.
*Color.*—Upper side — Dark Green with Brown Zonation. Under side — Green with a Brown Border.

THE BUD

Size: Small and long.
*Diameter.*—About 6 mm.
*Length.*—About 15 mm.
Shape: Ovoid and pointed.
Opening rate: Rapid.
Colors of petals:
*When sepals first divide.*—Red.
*When petals begin to unfurl.*—Red.
Sepals:
*Number.*—5.
*Shape.*—Long and pointed.
*Character.*—The sepals stand up when the florets open.
*Color.*—Inside — Reddish Brown. Outside — Brown.
Calyx:
*Shape.*—Broad.
*Aspect.*—Smooth.
*Splitting.*—Calyx does not split.
Peduncle:
*Length.*—14-16 cm.
*Character.*—Erect.
*Color.*—Brown.

INFLORESENCE

Blooming habit: Medium from early Spring to Mid-Fall.
Size of flower: Very large.
Borne: As a cluster of florets om a strong stalk.
Florets:
*Diameters.*—In average about 5.2 cm.
*Depth.*—In average about 6 mm.
*Number.*—About 50-60.
Petalage:
*Number.*—About 5.
*Form.*—Medium broad with small crinated margins.

*Arrangement.*—Arranged like the wings of a windmill.
*Texture.*—Soft.
*Appearance.*—Satiny.
*Color.*—41A on the body and on the base of the petal. 54C on the reverse side of the petal.

Flower stem:
*Length.*—About 4.5 cm.
*Color.*—Dark Brown.

Persistence: The petals stay on the stems about 4 days. The petals fall down when the flower matures.

Lasting quality: About 20 days.

Resistant to: Botrytis.

THE REPRODUCTIVE ORGANS

Stamens:
*Number.*—About 5.
*Arrangement.*—About the ovaries.

Anthers:
*Size.*—2.1 mm.
*Color.*—Red.

Filament:
*Length.*—About 7 mm.
*Color.*—White and Pink.

Pollen:
*Color.*—Orange.

Pistils:
*Number.*—1.

Styles:
*Length.*—About 10 mm.
*Color.*—Green and Pink.

Stigmas:
*Color.*—Red.

Fruit:
*Fertility.*—The fruit is fertile.
*Shape.*—Ovoid.
*Color at maturity.*—Dark Brown.

The huge vermilion flower clusters are long lasting on this geranium. They do not fade with heat, and they contrast greatly with the surrounding dark foilage.

I claim:

1. The new and distinctive geranium variety and the parts thereof, substantially as herein shown and described, characterized by its large vermilion flower clusters, which are long lasting.

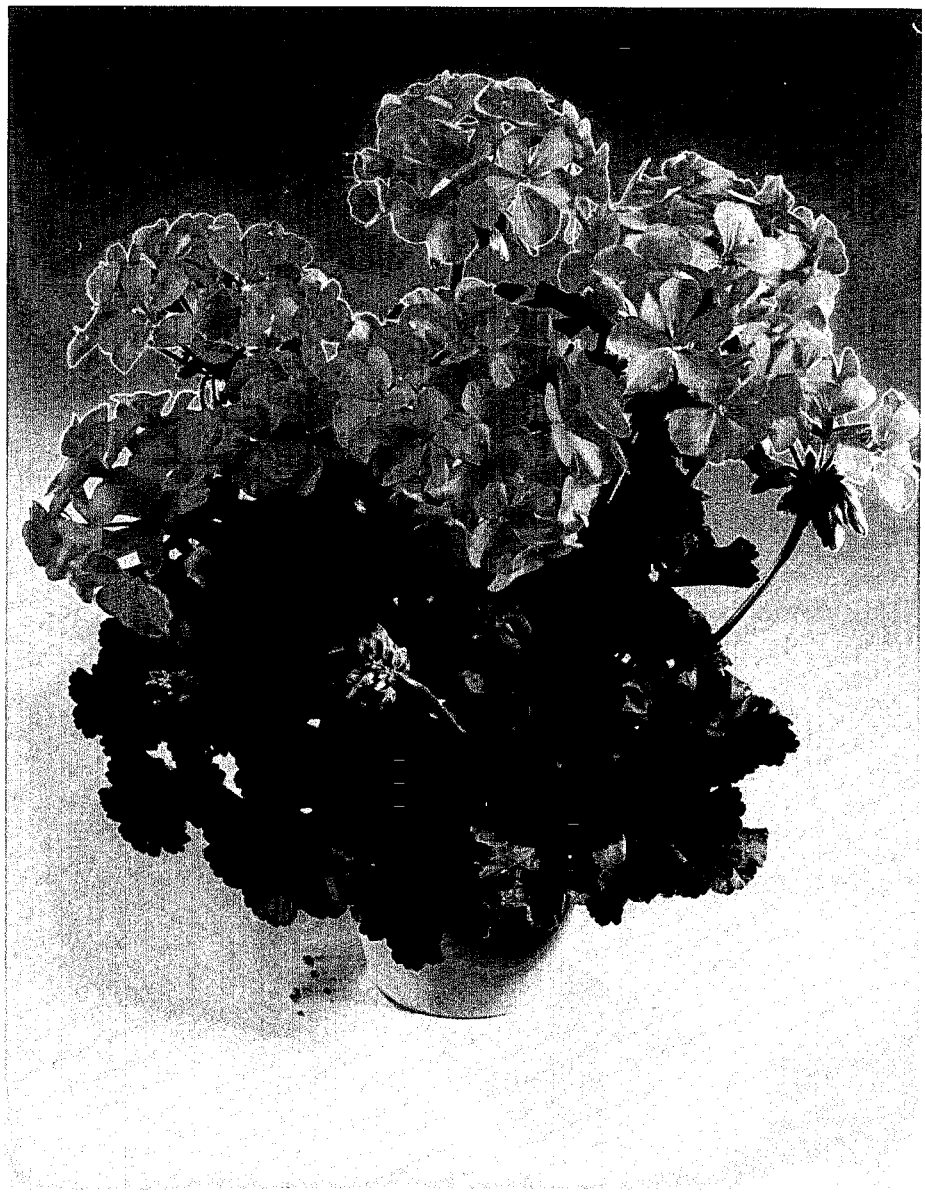

* * * * *